United States Patent
Koumans

(10) Patent No.: US 9,987,222 B2
(45) Date of Patent: Jun. 5, 2018

(54) METHOD FOR ADMINISTRATION OF A PROBIOTIC

(71) Applicant: BIOCLIN BV, Delft (NL)

(72) Inventor: Floris Koumans, Delft (NL)

(73) Assignee: BIOSOMA B.V., Delft (NL)

( * ) Notice: Subject to any disclaimer, the term of this patent is extended or adjusted under 35 U.S.C. 154(b) by 14 days.

(21) Appl. No.: 14/372,600

(22) PCT Filed: Jan. 30, 2013

(86) PCT No.: PCT/EP2013/051821
§ 371 (c)(1),
(2) Date: Jul. 16, 2014

(87) PCT Pub. No.: WO2013/113767
PCT Pub. Date: Aug. 8, 2013

(65) Prior Publication Data
US 2014/0358092 A1  Dec. 4, 2014

(30) Foreign Application Priority Data

Jan. 31, 2012 (EP) .................................... 12153401

(51) Int. Cl.
| | | |
|---|---|---|
| A61K 9/00 | (2006.01) | |
| A61K 35/747 | (2015.01) | |
| A61K 35/741 | (2015.01) | |
| A61M 31/00 | (2006.01) | |
| A61K 9/48 | (2006.01) | |
| A61K 9/06 | (2006.01) | |

(52) U.S. Cl.
CPC .......... *A61K 9/0034* (2013.01); *A61K 35/741* (2013.01); *A61K 35/747* (2013.01); *A61M 31/007* (2013.01); *A61K 9/06* (2013.01); *A61K 9/4841* (2013.01)

(58) Field of Classification Search
CPC .. A61K 35/741; A61K 9/0034; A61K 35/747; A61K 9/06; A61K 9/4841; A61M 31/007; A61M 31/00; A61M 2210/1475; A61F 13/26
USPC ................................ 604/212; 424/93.4, 451
See application file for complete search history.

(56) References Cited

U.S. PATENT DOCUMENTS

| | | | | |
|---|---|---|---|---|
| 7,064,114 B2 * | 6/2006 | Yiv | ...................... | A61K 9/0034 514/23 |
| 2002/0090365 A1 | 7/2002 | Chrisope | | |
| 2003/0229335 A1 * | 12/2003 | Payne | .................. | A61K 9/0036 604/890.1 |
| 2004/0092906 A1 | 5/2004 | Tosato | | |
| 2008/0262407 A1 * | 10/2008 | Chase | .................... | A61F 13/26 604/12 |
| 2010/0092440 A1 | 4/2010 | Strozzi | | |

OTHER PUBLICATIONS

"Room Temperature." The American Heritage Dictionary of the English Language. Eds. The Editors of the American Heritage Dictionaries. Boston: Houghton Mifflin, 2011. Credo Reference.*

(Continued)

*Primary Examiner* — Sean C. Barron
(74) *Attorney, Agent, or Firm* — Blank Rome LLP

(57) ABSTRACT

The present invention relates to a method for the administration of a probiotic composition to a vaginal cavity and to compositions, devices and kits for use in this method.

6 Claims, 4 Drawing Sheets

(56) References Cited

OTHER PUBLICATIONS

Figure 1A:
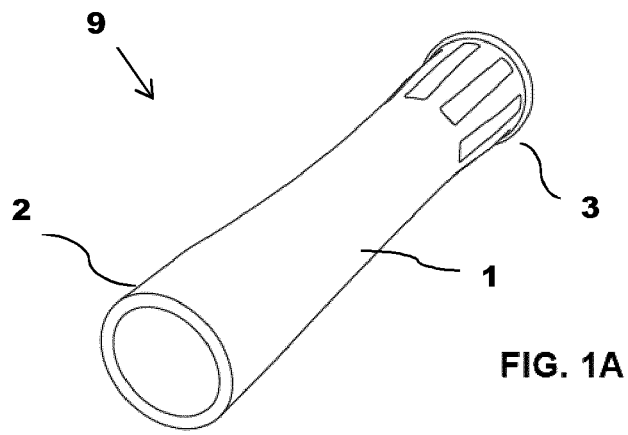

Brookfield support webpage (2006), from Internet Archive; 5 pages.*
International Search Report dated Mar. 5, 2013; International Application No. PCT/EP2013/051821; International Filing Date: Jan. 30, 2013; 3 pages.

* cited by examiner

METHOD FOR ADMINISTRATION OF A PROBIOTIC

FIELD OF THE INVENTION

The present invention relates to a method for administration of a probiotic, in particular to a method for local administration of a probiotic into the vagina in order to improve the vaginal health. It also relates to a kit and applicator for use in this method.

BACKGROUND OF THE INVENTION

A healthy vaginal flora is characterized by an acidic environment inhabited predominantly by lactic acid bacteria, primarily species of *Lactobacillus*. The species distribution differs between women of different geographical background, race, age, life style and so on. The vaginal Lactobacilli are believed to have a protective effect against vaginal colonisation by pathogenic microorganisms. The exact mechanism is not known, but the maintenance of a pH of approximately 4, in which few other microorganisms can survive, seems to play an important role.

However, several factors may contribute to the disturbance of the vaginal flora. A well-known factor is antibiotic therapy, which aims to kill pathogenic bacteria, but which is known to significantly reduce the amount of Lactobacilli in the vagina. Another important factor are hormonal changes, in particular changes in estrogen levels, which are observed in several phases of a woman's life, for example in the peri-menopausal period. Also pH increases, for example due to sexual intercourse, may disturb the vaginal flora, since other bacteria may start to flourish once the vaginal pH increases. Disturbance of the vaginal flora may lead to vaginal disorders, in particular to (vulvo)vaginal candidiasis and bacterial vaginosis, which are two common vaginal disorders which affect many women worldwide.

Vaginal candidiasis is a yeast infection of the vagina involving overgrowth of the yeast *Candida albicans*. It is frequently observed after antibiotic treatment, which reduces the population of Lactobacilli. Bacterial vaginosis is characterised by a depletion of vaginal Lactobacilli accompanied by an overgrowth of a mixed vaginal flora of other bacteria. It may increase a woman's susceptibility to other vaginal problems, infections, pre-term labour and HIV.

The vaginal flora can be restored by replenishing or supplementing the disturbed vaginal flora with acid producing bacteria from an external source. These compounds comprising beneficial live bacteria, in particular lactic acid producing bacteria, such as Lactobacilli, are the so-called probiotic compounds. For example, WO 03/080813 describes novel *Lactobacillus* strains which can be used in absorbent products or vaginal capsules to restore vaginal flora. WO 98/47374 describes *Bacillus* spores for vaginal application.

Alternatively, the vaginal flora may be restored by prebiotics, which are nutrients for the probiotics and which selectively promote the growth of probiotics, because these nutrients are not, or not readily, digested by other microorganisms. Oligosaccharides, in particular fructooligosaccharides, are well-known prebiotics. EP 0 591 443 describes a vaginal gel containing specific oligosaccharides for restoring the vaginal flora. The vaginal flora may also be restored by agents which improve the environmental conditions for probiotic growth or which inhibit the growth or adhesion to the host tissues of pathogens. EP 2 343 088 describes a vaginal suppository which contains an anti-mycotic to inhibit the growth of pathogenic fungi. US 2011/0098357 and EP 0 257 007 describe a vaginal suppository comprising lactic acid for restoring the vaginal pH and thus restoring the vaginal flora.

Prebiotic and probiotic therapy may be combined for a synergistic effect. WO 97/29762 describes synbiotic formulations for vaginal use, such as capsules, tablets and suppositories. WO 03/080813 describes synbiotic vaginal capsules. Using these synbiotics, probiotic colonisation should be achieved faster than when only prebiotics or probiotics are provided, because the probiotics provided do not have to compete for nutrients in the vagina.

Vaginal synbiotics in dry form have the disadvantage that they are dependent on the limited moisture in the vagina to dissolve and reach their full efficacy. On the other hand, it is not desirable to provide these synbiotics in liquid form, because probiotics are moisture-sensitive and moisture will limit the shelf life of the probiotic product.

SHORT DESCRIPTION OF THE FIGURES

Figure 1B:
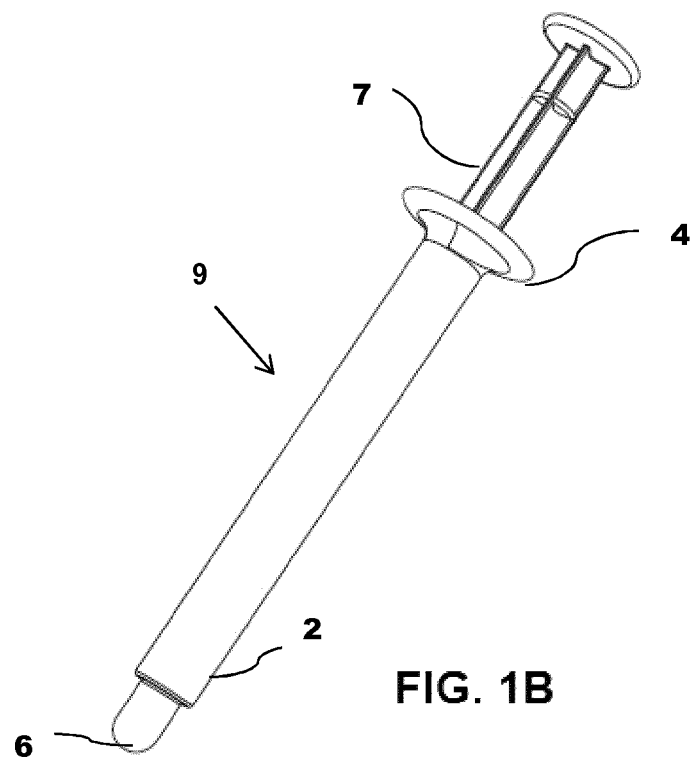

FIG. 1 Two applicators 9 which may be used in the method according to the invention. The applicators have a tube 1 with proximal end 2, which enters the vagina, and a distal end 3. FIG. 1B shows a piston-like applicator with a piston 7 and flange 4. The probiotic 6 is inserted at the proximal end 2.

FIG. 2 One embodiment of the invention, wherein the probiotic composition 6 and the growth supporting factor in a container 8 are received at the same end.

Figure 3:
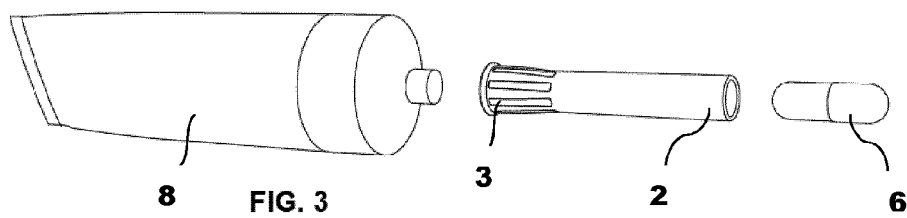

FIG. 3 Another embodiment of the invention, wherein the probiotic composition 6 and the growth supporting factor in a container 8 are received at different ends of the applicator.

Figure 4A:
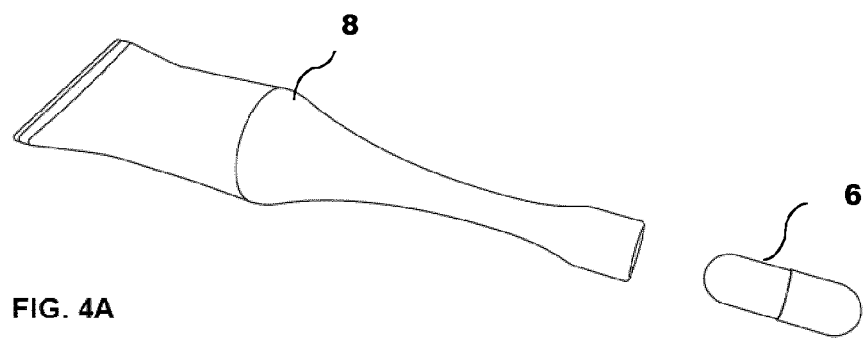
Figure 4B:
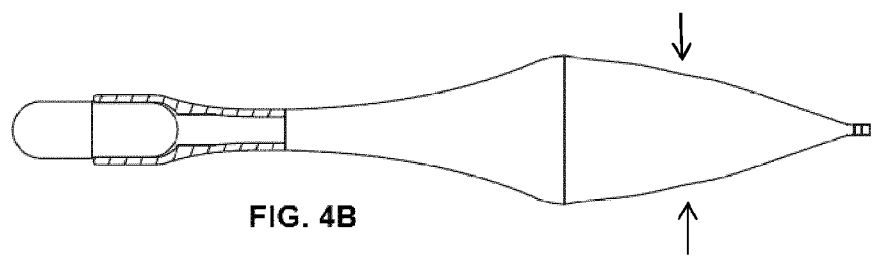

FIG. 4 Another embodiment of the invention, wherein the applicator is integrally formed from the container 8 containing the growth supporting factor 5 and which has a proximal end which is suitable for holding the probiotic composition 6. When pressure (indicated by arrows in FIG. 4B) is applied to the container 8 both growth supporting factor and probiotic composition 6 are expelled.

Figure 5:
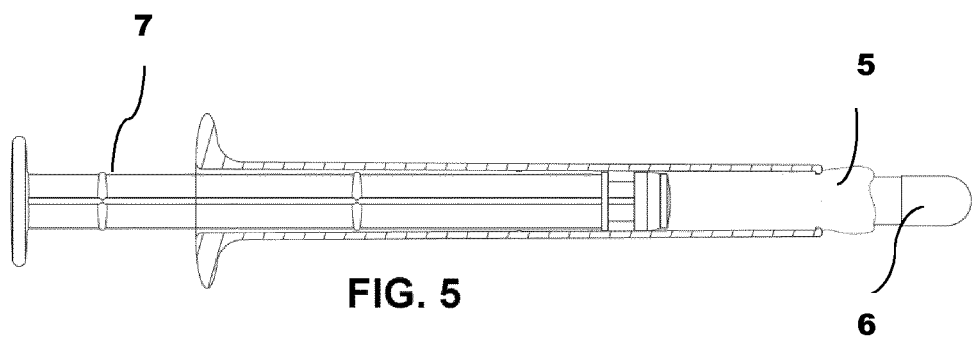

FIG. 5 A cross-section of one embodiment of the invention, in which an applicator with piston 7 and flange 4 is used to administer a probiotic 6 and growth supporting factor 5.

DETAILED DESCRIPTION OF THE INVENTION

The present invention relates to a method for the administration of a probiotic composition to the vagina. The method comprises administering the probiotic composition together with a growth supporting factor, such as a prebiotic composition or an acidic gel, to the vagina, whereby the probiotic composition and the growth supporting factor, such as the acidic gel or prebiotic composition, come into contact with each other just prior to or upon administration of the probiotic composition into the vagina. Preferably, an applicator is used to administer the probiotic composition into the vaginal cavity.

Since probiotic composition and growth supporting factor come into contact just prior to or upon administration of the probiotic composition into the vagina, the delivery of an adequate number of viable probiotic cells to the vaginal flora is ensured. By keeping probiotic and growth supporting factor separately until the moment of administration into the vagina, the probiotic composition and growth supporting factor interact, leading to activation of the probiotics by the growth supporting factor once they are in the vaginal cavity.

This is not the case when probiotic composition and growth supporting factor are premixed long before administration, because in such cases probiotics are activated while stored on the shelf and part of the probiotic cells will have died before administration to the vagina. This is particularly the case, when these mixtures have a high moisture content. In the present context, the term 'activation' refers to growth and multiplication of the probiotics and typically involves rehydration of the probiotics.

In contrast to state of the art methods which provide probiotics only, the method according to the invention provides the probiotics in the probiotic composition together with favourable growing conditions, nutrients or a combination of these elements. Probiotic composition and growth supporting factor are administered simultaneously or almost simultaneously. This supports the viability and stimulates growth and propagation of the probiotics provided. Thus another advantage of the method according to the invention is that the viability of the probiotic composition is supported and its impact maximised. The method is even more effective if the growth supporting factor selectively supports the probiotic organisms and not any pathogenic organisms, for example by specifically blocking pathogenic organisms.

In the context of the present application, the term 'probiotic composition' refers to a supplement which comprises viable bacteria and which improves or restores the vaginal flora. The vaginal flora may belong to any female, human or animal.

Any probiotic composition known in the art and suitable for vaginal application may be used in the method according to the invention. Probiotic compositions are well-known in the art. They typically include lactic acid producing bacteria, in particular genera of lactic acid bacteria, which have lactic acid as their main end product, such as selected strains of Lactobacilli, including *L. acidophilus, L. jensenii, L. gasseri, L. iners, L. delbrueckii, L. plantarum, L. crispatus, L. casei, L. fermenturn, L. reuterii, L. brevis, L. salivarius, L. johnsonii L. rhamnosus*; and selected strains of Bifidobacteria, including *B. bifidum, B. brevi, B. adolescentis* and *B. longum*, including mixtures of the mentioned strains. Other lactic acid producing bacteria which have been described as probiotics for vaginal application include species form *Bacillus*, such as *B. subtilis* and *B. coagulans*.

The probiotic composition may be in any form which is suitable for vaginal application. Preferably, the probiotic is in a dry form, such as a powder, a lyophilisate, a spore, a suppository or ovule, a tablet, a granulate or capsule. In dry form the viability and efficacy of the probiotic organisms at the time of application is best ensured. Ovule, tablet or capsule are typically about 2-4 cm in length and may be packed in a suitable packaging, for example in a bottle, flacon or blister pack. In one embodiment, the probiotic composition is in dry form, preferably a powder, more preferably a freeze-dried powder, and contained in a capsule. Any capsule which is suitable for vaginal application may be applied, such as PVA, gelatin or vegetable cellulose capsules, as long as the capsule readily dissolves inside the vagina. Since probiotic organisms are heat-sensitive and sensitive to pressure, tablets and suppositories are less preferred, because the heat and pressure involved in their preparation may damage the probiotic composition. If such formulations are used for formulation of the probiotic composition, measures should be taken to reduce the impact of the heat and pressure on the probiotic organisms. In a preferred embodiment, the probiotic composition is an encapsulated powder, preferably supplied in a blister pack.

A suitable dosage form of the probiotic composition allows for the application of at least $10^5$ colony forming units (cfu), more preferably, between about $10^5$ and about $10^{13}$ cfu, most preferably between about $10^7$ and about $10^{11}$ cfu per gram or per application.

The probiotic composition which is used in the method according to the invention may be contained in a container. The container may be any container which can be conveniently used in the method according to the invention. The container is preferably suitable for holding a dry powder. The container may be formed integrally from or be attached, detachably or permanently, to an applicator, if an applicator is used for the application of the probiotic composition.

In the present context, the term 'growth supporting factor' refers to any composition which supports or facilitates the growth of probiotic organisms, in particular in the vaginal cavity. Growth supporting factors typically include prebiotic compositions and other growth supporting compositions which provide good conditions for the probiotics in the probiotic composition for growing and colonizing the vaginal cavity. Preferably, the growth supporting factor interacts with and activates the probiotics in the probiotic composition only once in the vaginal cavity.

In one embodiment, the growth supporting factor consists of or comprises one or more prebiotic compositions. In another embodiment, the growth supporting factor consists of or comprises a mixture of one or more other growth supporting compositions. In yet another embodiment, the growth supporting factor consists of or comprises a mixture of one or more prebiotic compositions and one or more other growth supporting compositions.

The growth supporting factor may be combined with anti-fungal compositions, such as polyene e.g. nystatin and natamycin and imidazole antifungals, e.g. flucanozole and clotrimazole. In one embodiment, the growth supporting factor is a prebiotic acidic gel comprising an antimycoticum composition.

In the context of the present application, the term 'prebiotic composition' refers to a composition, which comprises or consists of prebiotics. A prebiotic is a compound which stimulates growth and development of probiotic microorganisms by acting as a substrate for these organisms. In the vagina, the prebiotics may stimulate both the probiotics administered and the beneficial flora already present in the vagina. The prebiotic composition may comprise between 0.001% and 100% w/w of prebiotics based on total weight of the prebiotic composition. In one embodiment, the prebiotic composition comprises between 1% and 90% w/w of prebiotics based on total weight of the composition. In another embodiment, the preparation comprises between 3% and 90% w/w of prebiotics based on total weight of the composition. In yet another embodiment, the preparation comprises between 1% and 30% w/w of prebiotics based on total weight of the composition. Prebiotics mainly consist of saccharides and soluble fiber, in particular fructooligosaccharides (FOS) or a glucooligosaccharides (GOS), inuline, glycogen, lactose and lactulose. The prebiotic composition may also comprise a mixture of several different prebiotics. In one embodiment, the prebiotic composition specifically favours the growth of the probiotic organisms or the desired vaginal flora, and not the growth of *Candida* or Gram negative pathogenic bacteria. One example of a prebiotic composition which specifically favours the growth of probiotic bacteria and not the growth of *Candida* or Gram negative pathogenic bacteria is a prebiotic composition consisting of FOS or GOS.

Examples of other growth supporting compositions include compounds which stimulate growth of the probiotic organism by improving the conditions with respect to moisture, pH, tonicity or energy and which are not prebiotics in the strict sense of the word. Any growth supporting composition suitable for vaginal application known in the art may be used in the method according to the present invention. A growth supporting composition suitable for the vagina will provide moisture, which will be beneficial for the probiotics, which are preferably activated by hydration or rehydration.

The growth supporting factor may comprise between 0.001% and 100% w/w of prebiotics and/or other growth supporting compositions based on total weight of the growth supporting factor. In one embodiment, the growth supporting factor comprises between 1% and 90% w/w of prebiotics and/or other growth supporting compositions based on total weight of the growth supporting factor. In another embodiment, the growth supporting factor comprises between 3% and 90% w/w of prebiotics and/or other growth supporting compositions based on total weight of the growth supporting factors. In yet another embodiment, the growth supporting factor comprises between 1% and 30% w/w of prebiotics and/or other growth supporting compositions based on total weight of the growth supporting factors.

The growth supporting factor is a liquid with a viscosity between 0.5 and 40 Pa·s., preferably between about 1 and about 20 Pa·s, measured at 19-21 degrees Celsius and at a spindle 4-7 at 12 rpm or spindle 4-7 at 20 rpm using a Viscometer & Model Brookfield DV-II+ Programmable. This prevents discharge of the growth supporting composition immediately after administration to the vagina and it allows the growth supporting factor to stay in the vagina long enough to allow activation of the probiotics. The growth supporting factor is preferably of a viscosity which allows the majority of it to stay in the vagina for at least 5 minutes, at least 10 minutes, at least 20 minutes, at least 30 minutes, when the vagina is in upright position, although the method according to the invention is preferably applied in horizontal position, i.e. while lying. It may be a liquid, an emulsion, a cream, a paste or a gel, including thermoreversible gels which are liquid at room temperature and a gel at body temperature. More preferably, the growth supporting factor is a liquid with a viscosity between about 8 and about 18 Pa·s, even more preferably a viscosity between about 7 and about 10 Pa·s at 19-21 degrees C. In one embodiment, the growth supporting composition is a gel. Preferably, the gel has a viscosity of between about 8 and about 18 Pa·s, more preferably a viscosity between about 7 and 10 about Pa·s at 19-21 degrees Celsius and at a spindle 4-7 at 12 rpm or spindle 4-7 at 20 rpm using a Viscometer & Model Brookfield DV-II+ Programmable.

The pH of the growth supporting factor is between about 3.5 and 5.5, preferably between about 3.5 and about 4.5. This may be achieved using an acidic buffer. Preferably, the growth supporting factor is isotonic. In one embodiment, the growth supporting composition comprises compounds which specifically favour the probiotic or the desired vaginal flora, and which do not favour the growth of or which block or inhibit *Candida* or Gram negative pathogenic bacteria. One example of growth supporting factor which specifically favours the growth of probiotic bacteria and not the growth of *Candida* or Gram negative pathogenic bacteria is an acidic gel.

The growth supporting factor, such as a prebiotic composition or another growth supporting composition, such as an acidic gel, are contained in a container. The container comprising the growth supporting factor may be any kind of container which can suitable hold a liquid, in particular a liquid with a viscosity of between 0.5 and 40 Pa·s. preferably between about 1 and about 20 Pa·s, measured at 19-21 degrees Celsius and at a spindle 4-7 at 12 rpm or spindle 4-7 at 20 rpm using a Viscometer & Model Brookfield DV-II+ Programmable. Therefore, the container comprising the growth supporting factor is preferably a bottle or a flacon, or a compressable container, such as a tube. The container may be formed integrally (see for example FIG. 4) from or attached, detachably or permanently, to an applicator which is used for the application of the growth supporting factor into the vagina. The container may hold one or more dosage volumes of the growth supporting factor. The amount of growth supporting factor which is applied to the vagina in the method according to the invention is typically in the range of about 1-3 ml, preferably about 2-3 ml. The container holding the growth supporting factor therefore preferably has a volume of between 4-6 ml, preferably 5 ml if it is a container which is discarded after single use, because there will always remain some product in the container. Alternatively, the volume of the container is at least 10 or 15 ml, preferably between 25 ml and 50 ml, if the container is used to supply multiple dosages.

In the method according to the invention, the probiotic composition and growth supporting factor come into contact which each other just prior to or upon application of the probiotic composition into the vagina. Preferably, the probiotic composition and growth supporting factor come into contact which each other less than 15, 10 or 5 minutes before or after vaginal application of the probiotic composition. More preferably, the probiotic composition and growth supporting factor come into contact which each other less than 4 minutes, less than 3 minutes, less than 2 minutes, less than 1 minute before or after vaginal application of the probiotic composition.

Most preferably, the probiotic and growth supporting factor are kept separately as long as possible to ensure that the growth supporting factor interacts with and activates the probiotics in the probiotic composition only once in the vaginal cavity. In one embodiment, the probiotics become activated by the growth supporting factor shortly after vaginal administration, for example within 15 minutes, within 10 minutes, within 5 minutes, 4 minutes, 3 minutes, 2 minutes, 1 minute, 50 seconds, 40 seconds, 30 seconds, 20 seconds or 10 seconds after vaginal application of the probiotic. In the context of the present invention, 'vaginal application' or 'vaginal administration' refers to insertion into, or further into, the vaginal cavity. It may refer to topical application to the mucosal or endometrial surfaces of the vagina. In the present context, the terms 'vagina' and 'vaginal cavity' are used interchangeably. Preferably, the application of probiotics, and their interaction with the growth supporting factor, is high in the vaginal cavity, near the vaginal fornices.

Vaginal application can be done in a quick, hygienic, effective and convenient way if an applicator is used for the application of growth supporting factor e.g. the prebiotic composition (or another growth supporting factor, such as an acidic gel). Any applicator known in the art and suitable for vaginal application may be used in the method according to the invention. In the Figures several embodiments of suitable applicators are shown. The applicator 9 used in the method according to the invention typically comprises a tube 1. The tube has a proximal end 2 and a distal end 3, whereby the proximal end 2 enters the vagina and the distal end 3 remains outside the vagina when used in the method according to the invention (FIG. 1). It may contain a flange 4 to prevent over-insertion into the vagina. The tube of the applicator is typically used for receiving and holding the growth supporting factor 5 shortly before it comes into contact with the probiotic composition 6. The applicator may contain a barrel 7, by which it becomes piston-like (FIG. 1B). The barrel 7 is used to expel the growth supporting factor 5 from the applicator into the vaginal cavity. In one embodiment, the growth supporting factor 5 which is expelled from the applicator is also used to drive the probiotic composition 6 into, or further into, the vaginal cavity (FIG. 5). In this way, the probiotic composition can conveniently be administered high in the vaginal cavity near the vaginal fornices. Using an applicator also makes it easier to ensure that the growth supporting factor interacts with and activates the probiotics in the vaginal cavity.

The applicator tube 1 is filled with growth supporting factor 5 from a container 8 holding the growth supporting factor. In one embodiment, the applicator tube is filled by emptying the whole or part of the content of the container containing the growth supporting factor 5 at the proximal end 2 of the applicator after connection of the applicator and the container 8. The container and applicator may be disconnected after the desired amount of growth supporting factor 5 has been transferred to the applicator (FIG. 2A-B).

In another embodiment, the applicator tube 1 is filled by emptying the whole or part of the content of the container 8 containing the growth supporting factor at the distal end 3 of the applicator, after connection of the applicator and the container. The container and applicator may be disconnected after the desired amount of growth supporting factor 5 has been transferred to the applicator (FIG. 3). Alternatively, the force which is used to expel the growth supporting factor 5 from its container into the applicator tube may be used to drive the probiotic composition into, or further into, the vaginal cavity. In this case, the connection between container 8 and applicator is maintained until the vaginal application of the probiotic composition 6 has been completed. In fact, the growth supporting factor 5 is used for vaginal application of the probiotic composition 6.

Figure 2A:
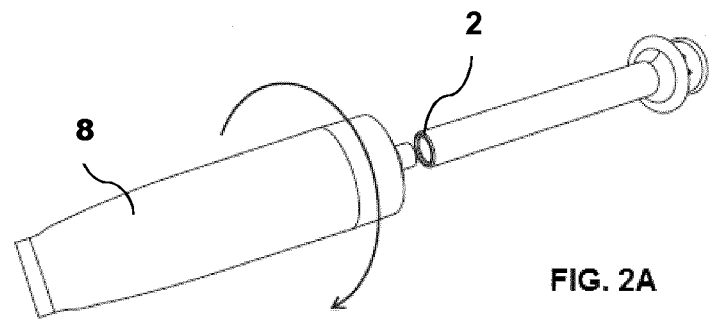
Figure 2B:
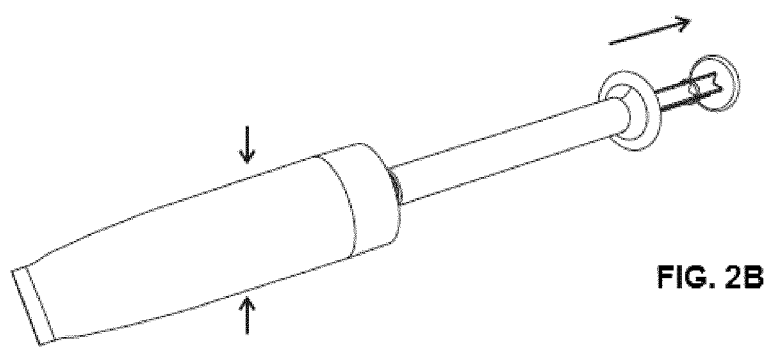
Figure 2C:
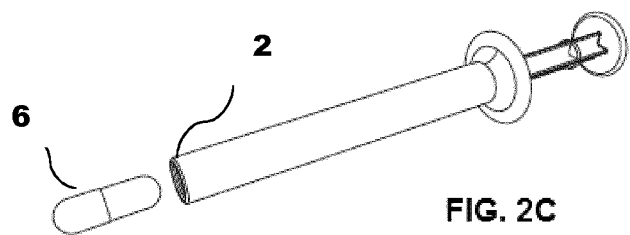
Figure 2D:
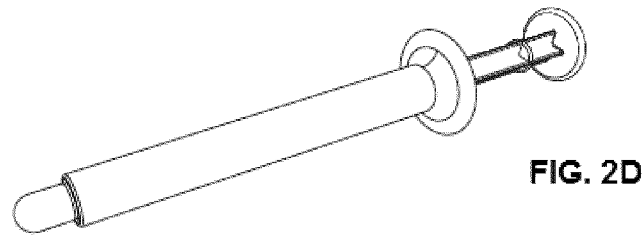

The connection between container and applicator may be made in any convenient way, for example by screwing one upon the other (FIG. 2A). Therefore, in one embodiment of the invention, a container 8 and applicator 9 with thread are used. The thread may be at the proximal end 2 or at the distal end 3 of the applicator 9.

Figure 4C:
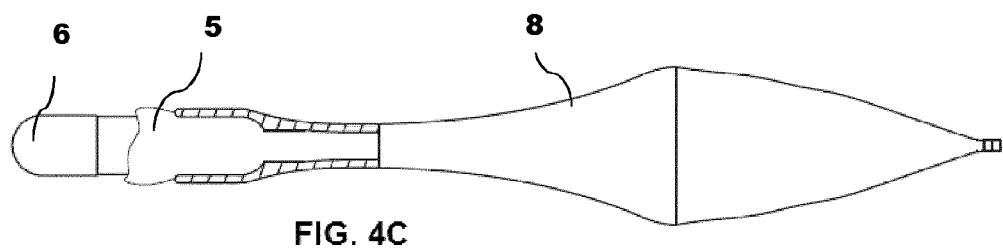

In yet an alternative embodiment, the container 8 containing the growth supporting factor and the applicator 9 are integrated as if the container is connected to the distal end 3 of the applicator (FIG. 4A-C). This may conveniently be combined with a monodose container which is discarded after one single use.

In yet another embodiment, the applicator is also suitable for receiving or holding both the probiotic composition 6 and the growth supporting factor 5. The growth supporting factor 5 and the probiotic composition 6 may be received at same ends, in which case they will be received sequentially, or at different ends, in which case they can be received sequentially or simultaneously. Preferably, the proximal end 2 of the applicator is suitable for receiving or holding the probiotic composition.

The proximal end 2 and distal end 3 may be designed the same, or may be different and they may have any form, preferably a form which makes reception of the growth supporting factor 5 or probiotic composition 6 convenient. In one embodiment, the proximal end 2 has a cup-like design, which allows for easy reception of the probiotic 6 (FIG. 4B). In another embodiment, the proximal end 2 has an inner thread, which allows for easy attachment to the container 8 containing the growth supporting factor 5.

If the applicator is calibrated, has a volume indication or maximal volume indication or control, this will make it more convenient and easy to use. It will prevent over-dosing and allows for economic and efficient use of the growth supporting factor.

The skilled person will understand that the above-mentioned embodiments, may be combined to form new embodiments. For example, the applicator which is integrated with the container holding the growth supporting factor may suitably be combined with a proximal end having a cup-like design, which allows for easy reception of the probiotic. The piston-like applicator may be combined with a volume indicator or volume control and a proximal end which is integrated with a container holding the dry probiotic composition.

Preferably, an applicator is used which is suitable for receiving both probiotic and growth supporting factor, whereby the growth supporting factor can be used to deliver the probiotic into the vaginal cavity. The applicator is preferably is suitable for delivering the probiotic composition high in the vaginal cavity near the vaginal fornices. The applicator preferably allows for activation of the probiotics in the vaginal cavity.

In one embodiment, this applicator is a tube-like applicator, 4-6 cm long, with an inner diameter of 0.5-0.8 cm at the proximal end for receiving the probiotic and an inner diameter of 0.7-0.9 cm at the distal end with a thread for connection to the container holding the growth supporting factor. In another embodiment, this applicator is a 9-12 cm long piston-like applicator with barrel having a tube with an inner diameter in the range of about 0.75 to 0.95 cm at the proximal end for receiving the probiotic and for receiving the growth supporting factor from its container.

The method according to the invention will differ slightly depending on which embodiment of applicator, growth supporting factor or probiotic composition is used.

In one embodiment, the method comprises:
(i) applying a probiotic composition to the vaginal cavity by hand;
(ii) inserting an applicator filled with a growth supporting factor into the vagina,
(iii) releasing the growth supporting factor from the applicator into the vaginal cavity, whereby the growth supporting factor and the probiotic composition come into contact with each other.

In the context of the present invention, 'application by hand' refers to application without an applicator. Instead of the applicator, one or more fingers are used to insert a probiotic composition into the vaginal cavity. Typically, the fingers will enter the vaginal cavity in the process. The skilled person will understand that steps (i), (ii) and (iii) may be in any order as long as the probiotic composition and the growth supporting factor or acidic gel come into contact which each other just prior to or upon application of the probiotic composition into the vagina.

In another embodiment, the method according to the invention is used for the vaginal administration of a probiotic composition, wherein the method comprises administering the probiotic composition in dry form together with an acidic gel or prebiotic composition in liquid form into the vaginal cavity, whereby the prebiotic composition or acidic gel comes into contact with the probiotic composition just prior to or upon application of the probiotic composition into the vaginal cavity. Preferably this is achieved by using an applicator which is suitable for keeping the growth supporting factor separate from the probiotic composition until in the vaginal cavity where the growth supporting factor, such as acidic gel or prebiotic composition, activates the probiotics in the probiotic composition. Activation is preferably by (re)hydration.

In another embodiment, the method according to the invention is used with an applicator which receives the growth supporting factor, such as prebiotic composition or acidic gel, and the probiotic composition at same ends, for example a piston-like applicator as depicted in FIG. 1B. The method then comprises:
(i) attaching a container containing the growth supporting factor to the proximal end of the applicator;
(ii) filling the applicator with the growth supporting factor from the container;
(iii) detaching the applicator from the container containing the growth supporting factor;
(iv) inserting the probiotic composition at the proximal end of the applicator;
(v) inserting the applicator, containing the growth supporting factor and the probiotic composition, in the vaginal cavity;
(vi) pushing in the piston of the applicator, whereby the probiotic composition and the growth supporting factor are released at the proximal end of the applicator into the vaginal cavity.

This embodiment of the method according to the invention is schematically represented in FIGS. 2 and 5. The applicator tube may have a volume or dosage indicator which indicates how much growth supporting factor is to be used. Alternatively, the piston of the syringe may be designed to block as soon as the required volume of growth supporting factor is transferred to the applicator.

In another embodiment, the method according to the invention is used with an applicator which receives the growth supporting factor and the probiotic composition at different ends, for example an applicator as depicted in FIG. 3. The method according to the invention then comprises:
(i) attaching a container containing the growth supporting factor to the distal end of the applicator;
(ii) filling the applicator with the growth supporting factor from the container;
(iii) placing the probiotic composition into the proximal end of the applicator;
(iv) inserting the applicator in the vagina, and then
(v) releasing more growth supporting factor from the container at the distal end, whereby the probiotic composition is released into the vaginal cavity together with some of the growth supporting factor.

The skilled person will understand that steps (i), (ii) and (iii) may be in any order, as long as the probiotic composition and growth supporting factor come into contact which each other just prior to or upon application of the probiotic composition into the vagina. If more convenient, the applicator may be filled with the growth supporting factor from the container until the growth supporting factor is just visible at the proximal end of the applicator. In these circumstances, activation of the probiotics may still be confined to the vaginal cavity, in particular when the probiotic composition is encapsulated, since in such a case contact will not immediately lead to activation. In any case, after release of the probiotic and the growth supporting factor, the applicator is removed from the vaginal cavity again. The applicator may be designed as a single use applicator, which is thrown away after each use. Alternatively, the applicator may be designed for multiple use, in which case it has to be cleaned, and optionally sterilised, after each use. Both single use and multiple use applicators are preferably designed from inert polymeric materials, such as polystyrene or polypropylene.

The probiotic and the growth supporting factor, such as a prebiotic composition or acidic gel, are used according to the manufacturer's instructions. Depending on the vaginal disorder which is to be treated or prevented, the method may be applied for several days, for example for 5-7 days, for several weeks, for example 2-4 weeks or several months, for example 1 to 3 months. Preferably, the method according to the invention is used until the vaginal disorder is cured. Depending on the vaginal disorder and the severity, the method according to the invention may be applied at least once a month, at least once a week, at least every other day or at least once a day. Vaginal disorders which may be prevented or treated are in particular bacterial vaginosis, candiasis and vaginitis, which are all examples of a disturbed vaginal flora.

In another aspect, the present invention relates to a growth supporting factor, such as a prebiotic composition or acidic gel, for use in a method for vaginal administration of a probiotic composition. The method comprising applying the probiotic composition together with a growth supporting factor into the vaginal cavity, whereby the probiotic composition and the growth supporting factor come into contact with each other just prior to or upon application of the probiotic composition.

Preferably, the growth supporting factor is applied in the vagina using an applicator. In one embodiment, the a prebiotic composition or acidic gel for use in a method for vaginal administration of a probiotic composition is applied into the vaginal cavity with the aid of an applicator, whereby the prebiotic composition or acidic gel activates the probiotics in the probiotic composition only once in the vaginal cavity.

The earlier-mentioned embodiments and preferred embodiments which were mentioned for the growth supporting factor, the probiotic composition and the applicator used in the method according to the invention are also applicable to the applicator, the probiotic composition and the growth supporting factor in this aspect. In a particularly preferred embodiment, the growth supporting factor interacts with and activates the probiotics in the probiotic composition only once in the vaginal cavity.

In yet another aspect, the present invention relates to an applicator for use in a method for vaginal administration of a probiotic composition, the method comprising applying the probiotic composition together with a growth supporting factor into the vaginal cavity, whereby the probiotic composition and the growth supporting factor come into contact with each other just prior to or upon application of the probiotic composition. The earlier-mentioned embodiments and preferred embodiments which were mentioned for the growth supporting factor, the probiotic composition and the applicator used in the method according to the invention are also applicable to the applicator, the probiotic composition and the growth supporting factor in this aspect. In a particular preferred embodiment, the applicator is used in a method for vaginal administration of a probiotic composition, whereby one applicator is used to deliver both the probiotic composition and the growth supporting factor, which factor interacts with and activates the probiotics in the probiotic composition only once in the vaginal cavity. The applicator preferably delivers the probiotic composition near the vaginal fornices.

In another aspect, the present invention relates to a kit comprising (i) a probiotic composition, and (ii) a growth supporting factor and optionally (iii) an applicator. This kit can suitably be used in the method according to the invention. The probiotic composition in the kit comprises viable bacteria which improve or restore the vaginal flora and is preferably present in dry form, more preferably in encapsulated dry form. The growth supporting factor in the kit is a composition which supports or facilitates the growth of the probiotic organisms. In a preferred embodiment, the growth supporting factor in the kit is a prebiotic composition or an acidic gel which is kept separately from the probiotic composition. The two only interact with each other once combined in the vaginal cavity.

The earlier-mentioned embodiments and preferred embodiments which were mentioned for the growth supporting factor, the probiotic composition and the applicator used in the method according to the invention are also applicable to the growth supporting factor, the probiotic composition and the applicator in the kit. Therefore, in one embodiment, the kit comprises a probiotic composition in dry and encapsulated form together with, but separately contained, a growth supporting factor in gel form and an applicator. The applicator may be suitable for the application of the growth supporting factor. The applicator may also be suitable for the application of the probiotic composition. The container holding the growth supporting factor or the probiotic composition may be integrated with the applicator. The applicator in the kit typically comprises a tube, optionally with a flange, and optionally with a barrel and allows for delivery of the probiotic compound near the vaginal fornices.

In one embodiment, the kit comprises (i) a probiotic composition in dry form and (ii) an acidic gel or prebiotic composition, wherein the acidic gel or prebiotic composition is a liquid with a viscosity of between about 1 Pa·s and about 20 Pa·s measured at 19-21 degrees Celsius and at a spindle 4-7 at 12 rpm or spindle 4-7 at 20 rpm using a Viscometer & Model Brookfield DV-II+ Programmable, and optionally (iii) an applicator which is suitable for administration of the probiotic composition high in the vagina near the vaginal fornices.

In another embodiment, the kit comprises (i) an encapsulated probiotic composition in dry form and (ii) a prebiotic composition with a viscosity of between 0.5 Pa·s and 40 Pa·s, preferably of between 1 Pa·s and 20 Pa·s, measured at 19-21 degrees Celsius and at a spindle 4-7 at 12 rpm or spindle 4-7 at 20 rpm using a Viscometer & Model Brookfield DV-II+ Programmable, and (iii) an applicator which is suitable for receiving the probiotic composition and the prebiotic composition at the same end of the applicator.

In another embodiment, the kit comprises (i) an encapsulated probiotic composition in dry form and (ii) a prebiotic composition with a viscosity of between 1 Pa·s and 20 Pa·s, measured at 19-21 degrees Celsius and at a spindle 4-7 at 12 rpm or spindle 4-7 at 20 rpm using a Viscometer & Model Brookfield DV-II+ Programmable, and (iii) an applicator which is suitable for receiving the probiotic composition and the prebiotic composition at the same end of the applicator.

In yet another embodiment, the kit comprises (i) an encapsulated probiotic composition in dry form and (ii) a prebiotic acidic gel with a viscosity of between 0.5 Pa·s and about 40 Pa·s, preferably of between 1 Pa·s and 20 Pa·s, measured at 19-21 degrees Celsius and at a spindle 4-7 at 12 rpm or spindle 4-7 at 20 rpm using a Viscometer & Model Brookfield DV-II+ Programmable which is contained in a compressable container, such as a tube, and (iii) an applicator which is suitable for receiving the probiotic composition and the prebiotic acidic gel at different ends of the applicator.

In yet another embodiment, the kit comprises (i) an encapsulated probiotic composition in dry form and (ii) an acidic gel or prebiotic composition, wherein the acidic gel or prebiotic composition is a liquid with a viscosity of between 1 Pa·s and 20 Pa·s measured at 19-21 degrees Celsius and at a spindle 4-7 at 12 rpm or spindle 4-7 at 20 rpm using a Viscometer & Model Brookfield DV-II+ Programmable, and is contained in a compressable container, such as a tube, with an applicator which is suitable for receiving the probiotic composition and the prebiotic composition or acidic gel at the same end of the applicator, whereby the applicator has volume indicators for applying proper amounts of prebiotic composition or acidic gel.

In yet another embodiment, the kit comprises, comprises (i) an encapsulated probiotic composition in dry form and (ii) a prebiotic composition or acidic gel with a viscosity of between 0.5 Pa·s and about 40 Pa·s, preferably of between 1 Pa·s and 20 Pa·s, measured at 19-21 degrees Celsius and at a spindle 4-7 at 12 rpm or spindle 4-7 at 20 rpm using a Viscometer & Model Brookfield DV-II+ Programmable, which is contained in a compressable container, such as a tube, and (iii) an applicator, wherein the applicator is suitable for keeping the probiotic composition separately from the acidic gel or prebiotic composition until in the vaginal cavity, where the acidic gel or prebiotic composition activates the probiotics in the probiotic composition by rehydration.

The kit may comprise single dosage forms or multidosage forms of the growth supporting factor or the probiotic composition. In one embodiment, the kit comprises at least two, preferably at least three, at least four or at least five, more preferably at least six, at least seven or at least eight, most preferably at least nine, at least ten or at least eleven small tubes for single use containing a growth supporting factor and at least two, preferably at least three, at least four or at least five, more preferably at least six, at least seven or at least eight, most preferably at least nine, at least ten or at least eleven dosage forms of the probiotic compound, together with an applicator for the vaginal application of the growth supporting factor.

In another embodiment, the kit comprises at least two, preferably at least three, at least four or at least five, more preferably at least six, at least seven or at least eight, most preferably at least nine, at least ten or at least eleven small tubes for single use containing a growth supporting factor, such as a prebiotic composition or an acidic gel, and at least two, preferably at least three, at least four or at least five, more preferably at least six, at least seven or at least eight, most preferably at least nine, at least ten or at least eleven dosage forms of the probiotic compound. Each small tube comprises a long tip ending in an end which is suitable to receive the probiotic compound dosage form, like an integrated applicator with a mouthpiece for the probiotic compound.

In yet another embodiment, the kit comprises at least two, preferably at least three, at least four or at least five, more preferably at least six, at least seven or at least eight, most preferably at least nine, at least ten or at least eleven dosage forms of the probiotic compound together with a tube holding the growth supporting factor, and a piston-like applicator which can be used to measure the volume of growth supporting factor squeezed from the tube. The contents of the tube is sufficient for several applications.

Using the earlier-mentioned embodiments and preferred embodiments for the method, growth supporting factor, the probiotic composition and the applicator, the skilled person will be able to ascertain other embodiments for the kit according to the present invention.

The applicator and the method of the invention may be applied to other body cavities, in particular mucosal cavities, including other cavities of the urogenital area, where disorders have to be treated or prevented in a patient. The patient may be male or female, human or animal.

The method and kit according the invention may suitably be used for other two components systems in which contact between a first and a second component is preferably regulated in time or space, e.g. a precursor and its activator. Typically, if the two components of such systems come into contact too early, i.e. before use or before the first component has arrived at its intended place of action, this will have a negative effect. The negative effect could be that early activation leads to lowered or insufficient action at the moment of actual use or at the intended site of use or it may lead to harmful effects.

EXAMPLES

Example 1 Kit Containing Probiotic Tablets and Lactic Acid Gel

A kit according to the invention may be used by a lady of 44 years of age who regularly suffers from Candidiasis; a vaginal fungal infection with itching, discharge and irritation. The kit contains a box with five 5 ml tubes with long thin ends and a strip with five tablets. The 5 ml tubes are for single use and contain a lactic acid gel, pH 4 which adjusts the vaginal pH value in order to improve growing conditions for lactic acid bacteria. The tablets contains freeze-dried Lactobacilli. The product is used for several days just before going to bed by first using the fingers to insert one of the probiotic tablets in the vagina, then inserting the tube containing the lactic acid gel into the vagina. The gel is thereby released and the tablet is pushed a bit further up into the vagina. The lactic acid gel stimulates the growth of the probiotic bacteria from the tablet and vaginal flora will be restored much earlier then when only tablets or only lactic acid gel is used. Vaginal application is a bit messy and may require cleaning fingers before and after applying the gel.

Example 2 Kit with Probiotic Capsules, and Prebiotic Gel with Integrated Applicator and End for Receiving Probiotic A kit according to the invention may be used by a lady of 30 years of age who has taken a course of oral antibiotics in relation to a sinusitis. The antibiotics may impact her vaginal flora and a probiotic composition can be used to supplement the Lactobacilli that normally colonize the vagina and are essential for vaginal health. The kit comprises five plastic tubes and a strip with five capsules. The capsules contain a probiotic powder containing lyophilized Lactobacilli together with some support ingredients. The capsules are a relatively large size of the typical gelatin capsules that are often used for antibiotics and other medications. The five tubes are monodose plastic tubes of 5 ml each. The tubes contain a prebiotic gel which contains nutrients for the Lactobacilli of the probiotic powder, such as glycogen and other sugar components, together with some amino acids and minerals. The gel has a pH value of 4. Each of those small plastic tubes has a long tip that has a special end to it. The end of this application tip is like a small cup intended to hold a capsule. She opens the tube by breaking off a plastic pin that seals the applicator on the tube. The capsule is placed in the cup-like holder-space at the end of the applicator. The applicator with the capsule placed at the end is entered into her vagina and the gel is squeezed out of the tube. The gel pushes out the capsule from the holder and in this way the probiotic capsule is entered into the vagina together with the prebiotic gel. This product has clear added value over vaginal gels because of the combination with the probiotics. Also, the monodose makes it easy to apply the right amount of gel in combination with the probiotic capsule and the capsule enters the vagina very easy because it is placed on the application tip of the tube.

Example 3 Kit with Probiotic Capsules, Acidic Gel and Multi-Dose Applicator

A kit according to the invention may be used by a lady of 50 who has received treatment for a cervix carcinoma. Since such treatments have severe impact on vaginal flora, the use of some kind of product to improve the flora and thus the vaginal health is advisable. The product was packed in a box with information leaflet and an aluminum tube of 25 ml containing a gel with pH 4. Also, the package holds a strip of 10 probiotic gelatin capsules and a special applicator. The applicator looks like a syringe and the top of this applicator can be placed on the tube. In this way the product from the tube can be squeezed into the applicator. The piston of the syringe is designed to block when the applicator holds 2 ml of the gel since this is a suitable volume for vaginal application. The applicator is taken off the tube and at the open end of the applicator one of the probiotic capsules can be placed. Like this, the applicator is entered into the vagina, with the gel inside the applicator and the capsule placed at the end of it. Inside the vagina the piston is pushed back and in this way the gel is pushed out of the applicator together with the capsule and the combination of the gel and capsule enters the vagina. Here the gelatin capsule dissolves because of the moisture of the vagina and the gel and releases the probiotic powder. The Lactobacilli in the powder are supported in their development by the gel that has been designed to create good conditions for growth of Lactobacilli. The plastic applicator has to be cleaned well with warm water for reuse. The kit is used in the evening prior to bedtime according to the manufacturer's instructions in the leaflet. The kit allows for an effective way of application. The amount of gel can be dosed conveniently and the product can be entered deep into the vagina to act.

Example 4 Kit with Probiotic Suppositories, Prebiotic Cream and Applicator

A kit according to the invention may be used by a lady of 25 years of age who regularly suffers from bacterial vaginosis; a condition of overgrowth of unwanted bacteria in the vagina. The symptoms are itching and a discharge with unpleasant odor. To increase her vaginal health and in this way reduce the recurrence of the bacterial problems a kit according to the invention may be used. It comprises a box with inside a product information leaflet, an aluminum tube of 20 ml content, a set of seven plastic cannulas and a strip with seven probiotic suppositories. The tube contains a vaginal cream that aims to reduce the growth of unwanted bacteria but does not affect the useful Lactobacilli; it also contains some nutrients for Lactobacilli and has a pH value of 4.5 in support of Lactobacilli. Each plastic cannula can be screwed on the opening of the tube. A cannula has an end with a hollow space that is ideally suitable to hold one of the suppositories. The suppositories look like the type often used for rectal application and are based on a glycerin like substance in which a probiotic powder consisting of freeze-dried Lactobacilli is mixed. For use, a cannula is screwed on the tube and a suppository is placed in the end of the cannula. The cannula with the suppository at the tip is inserted into the vagina and an ample amount of the cream is gently squeezed out of the tube. While squeezing the cream out of the tube also the suppository is released into the vagina. The cream and the suppository have a synergistic effect. While the cream suppresses the harmful bacteria the suppository introduces an amount of the useful Lactobacilli that are essential for a healthy vaginal flora. The product is used as a course of seven days both to treat the symptoms as well as to prevent the problem from reoccurring by establishing a healthy flora.

The invention claimed is:

1. A method for vaginal administration of a probiotic composition using an applicator, the applicator comprising a tube having a proximal and a distal end, the proximal end configured for introduction into a vaginal cavity during use, the tube adapted for expelling both a prebiotic composition and the probiotic composition from the proximal end; the method comprising the steps of:

transferring a prebiotic composition, in liquid form, to the applicator from a container separate from the applicator before placing a probiotic composition in the proximal end of the tube, wherein the container separate from the applicator is detachably attached to the proximal end of the tube;

placing the probiotic composition in encapsulated dry form in the proximal end of the tube of the applicator;

introducing the proximal end of the tube into a vaginal cavity;

forcing the prebiotic composition out of the proximal end of the tube, the prebiotic composition expelling the probiotic composition from the proximal end of the tube and into the vaginal cavity, the prebiotic composition interacting with, and activating, probiotics in the probiotic composition; and contacting mucosal or endometrial surfaces of the vagina with the activated probiotics, therein promoting probiotic growth and colonization in the vaginal cavity.

2. The method of claim 1, wherein the prebiotic composition has a viscosity of between 0.5 and 40 Pa·s measured at 19-21 degrees Celsius and at a spindle 4-7 at 12 rpm or spindle 4-7 at 20 rpm using a Viscometer & Model Brookfield DV-II+ Programmable.

3. The method of claim 1, wherein the prebiotic composition comprises an anti-fungal composition.

4. The method of claim 1, further comprising the step of placing the proximal end of the tube near the vaginal fornices before forcing the prebiotic composition out of the proximal end of the tube.

5. The method of claim 1, wherein the container separate from the applicator is detached from the applicator before the tube is introduced into the vaginal cavity.

6. The method of claim 1, wherein the prebiotic composition interacts with and activates the probiotics in the probiotic composition once in the vaginal cavity.

* * * * *